(12) United States Patent
Ulrich (10) Patent No.: US 6,375,898 B1
(45) Date of Patent: Apr. 23, 2002

(54) ANALYSIS SYSTEM (75) Inventor: Frank Ulrich, Moerlenbach (DE)

(73) Assignee: Start Diagnostics GmbH, Vierheim (DE)

(*) Notice: Subject to any disclaimer, the term of this patent is extended or adjusted under 35 U.S.C. 154(b) by 0 days.

(21) Appl. No.: 09/403,298

(22) PCT Filed: Feb. 19, 1999

(86) PCT No.: PCT/EP99/01092

§ 371 Date: Oct. 18, 1999

§ 102(e) Date: Oct. 18, 1999

(87) PCT Pub. No.: WO99/42841

PCT Pub. Date: Aug. 26, 1999

(30) Foreign Application Priority Data

Feb. 20, 1998 (DE) .......................................... 198 07 177

(51) Int. Cl.[7] .......................... G01N 35/02; G01N 35/10
(52) U.S. Cl. ............................ 422/64; 422/62; 422/63; 422/65; 422/66
(58) Field of Search ............................ 422/62, 63, 64, 422/65, 66; 436/45, 49, 54

(56) References Cited

U.S. PATENT DOCUMENTS

| | | | | |
|---|---|---|---|---|
| 4,046,511 A | * | 9/1977 | Stabile ........................ | 422/64 |
| 4,265,855 A | * | 5/1981 | Mandle et al. | |
| 4,751,186 A | * | 6/1988 | Baisch et al. | |
| 5,158,895 A | * | 10/1992 | Ashihara et al. | |
| 5,540,890 A | * | 7/1996 | Clark et al. ................. | 422/102 |
| 5,580,524 A | * | 12/1996 | Forrest et al. ................. | 422/63 |
| 5,876,668 A | * | 3/1999 | Kawashima et al. .......... | 422/64 |

FOREIGN PATENT DOCUMENTS

| | | | |
|---|---|---|---|
| DE | 3318573 A1 | * | 1/1984 |
| DE | 3639399 A1 | * | 5/1987 |
| DE | 2826876 C2 | * | 10/1987 |
| DE | 4013166 A1 | * | 10/1990 |
| DE | 4128698 A1 | * | 3/1993 |
| DE | 4312093 A1 | * | 10/1993 |
| DE | 19701505 A1 | * | 7/1997 |
| EP | 0217000 A2 | * | 4/1987 |
| EP | 0223002 A2 | * | 5/1987 |
| EP | 0410688 A2 | * | 1/1991 |
| EP | 0449321 A2 | * | 10/1991 |
| GB | 1432114 | * | 4/1976 |
| WO | WO 93/02364 | * | 2/1993 |

OTHER PUBLICATIONS

Product brochure for "Dimension Rx1" of the firm of Dade Behring.

* cited by examiner

Primary Examiner—Nina Bhat
(74) Attorney, Agent, or Firm—William Michael Hynes; Townsend and Townsend and Crew LPP (57) ABSTRACT

An analysis system, in particular for medical analysis work for carrying out clinical-chemical and immunological analyses, comprises an analysis appliance and at least one system-reagent carrier. The system-reagent carrier has at least one cuvette which is pre-filled with a test-specific, preformulated, wet-chemical system reagent, as well as the measuring cuvette.

34 Claims, 4 Drawing Sheets

ANALYSIS SYSTEM

This application claims benefit under 35 USC §371 of EP/01092 filed Feb. 19, 1999.

BACKGROUND OF THE INVENTION

The invention relates to an analysis system, in particular for medical analysis work for carrying out clinical-chemical and immunological analyses.

Wet-chemical analysis systems, in which liquid reagents are provided in reagent containers which are held in suitable holders of a rotatable reagent rotor, are known. Furthermore, these known wet-chemical analysis systems have a sample rotor into which the samples contained in corresponding sample tubes are inserted. The reagent rotor is assigned a reagent pipettor, and the sample rotor is assigned a sample pipettor. A third rotor, a reaction rotor, is fitted with reaction cuvettes.

These known wet-chemical analysis systems operate as follows: the reagent pipettor is used to remove a predetermined amount of an analysis-specific reagent from the reagent containers contained in the reagent rotor and introduce this into a reaction cuvette, whereupon the sample pipettor removes a specified amount from a predetermined sample and introduces it into the reaction cuvette which has been filled with the reagent. The reaction cuvette, which in this way has been fed with a reagent and a sample, is moved from the reaction rotor to a measurement position, where, for example, a photometric measurement of the reaction solution is carried out, which is then evaluated on the basis of stored comparison values.

Wet-chemical analysis systems of this nature are suitable in particular for extensive series of tests or for a high incidence of analysis, as arises, for example, in clinical laboratories. Since the wet-chemical reagents contained in the open reagent vessels in the reagent plate have only a limited shelf life, a wet-chemical analysis system of this nature can only be operated if a certain minimum number of examinations are carried out in the system, since otherwise excessively frequent exchanging of reagents which have not been used but have expired is required, and this increases the operating costs.

As an alternative, a dry-chemical analysis system, in which reagents are applied to a carrier material in the solid state, is known. These reagent carriers are wetted with a predetermined amount of the sample, and the reagent carrier to which the sample has been applied is then examined in a detector device, for example by means of photometric measurement. However, these dry-chemical analysis systems have the drawback that the development costs for the reagent carriers are very high and that the samples generally have to be applied manually to the reagent carrier, so that these analysis systems are only suitable for single measurements or measurements with small numbers of samples or tests.

DE 33 18 573 A1 has disclosed an analysis appliance in which two concentrically rotatable rotors, i.e. an inner rotor for sample cuvettes and an outer rotor for measuring cuvettes, are provided, which rotors can be rotated independently of one another. Furthermore, in this appliance there is a pivotable working arm which, at its free end, is provided with a pipette. The pivot path of the pipette intersects the two rotors, so that in each case one measuring cuvette of the outer rotor and one sample cuvette of the inner rotor lie in the pivot path of the pipette. Furthermore, a measuring station, reagent bottles and a device for drying the pipette, as well as, if appropriate, a cleaning station for the pipette, are provided on the pivot path of the pipette, outside the outer rotor.

This known device operates as follows:

The arm with the pipetting device is pivoted over a sample cuvette located in the inner rotor, the pipette tip is immersed in the sample, and the sample is drawn into the pipette. The arm then pivots from the inner rotor to the outer rotor, above a measuring cuvette, and releases the sample into the measuring cuvette. Then, the measuring cuvette is taken hold of by a gripper situated on the arm, is lifted together with the arm, removed from the rotor and pivoted over the stationary measuring station, whereupon the measuring cuvette is lowered into the measuring station and released by the gripper. After this, the arm executes one or more further sequences of movements and, if appropriate after the pipette has first been cleaned, picks up one reagent or a plurality of reagents from the stationary reagent bottles, which are then injected into the measuring cuvette located in the measuring station. After the measurement has taken place, the measuring cuvette is returned to its position in the outer rotor by the arm.

A drawback of this known device is that the measuring cuvettes have to be transported out of and back to the rotor by the arm, making it necessary to provide the arm with a gripper, and consequently the arm structure becomes complex.

Furthermore, transporting the measuring cuvette from the outer rotor to the measuring station by means of the arm requires a certain time, during which the analysis appliance is not available for its actual task, i.e. for analysis.

DE 41 28 698 A1 has disclosed an analysis system in which sample vessels, reagent vessels and reaction vessels are arranged on a common rotor. This analysis system is equipped with a lifting pipettor which is arranged above the rotor edge and is able, by being lowered and raised, to pipette samples and reagent to and fro between different positions on the rotor, which rotates for this purpose. A photometric measuring station, which is able to carry out measurements on a fluid contained inside a reaction vessel in the rotor, is provided radially outside the rotor. The reagent vessels on the rotor of this known analysis system are formed by storage containers which are provided with dispensing openings, which the pipette tip of the pipetting arm can enter. Owing to the arrangement of the reagents on the rotor, and in particular within relatively large storage containers on the rotor, the number of reagents which can be used and/or the number of samples which can be analyzed is limited by the space available on the rotor, so that an analysis system of this nature can be used primarily for standardized, recurring tests which always use the same reagents.

EP 0,223,002 A2 has disclosed an automatic analysis system in which reagent carriers which are each provided with a plurality of holders are used. One of these holders serves as a measuring cuvette, one serves as a sample holder, and the other holders contain reagents. A plurality of reagent carriers are held next to one another in a magazine which can move in translation, it being possible to move the reagent-carrier holders of the magazine to in front of the entrance to a transfer station. The exit of the transfer station is directed towards spoke-like reagent-carrier holders of a rotary wheel. A system-reagent carrier which has been moved out of the magazine into the transfer station is processed in the transfer station, for which purpose pipetting and suction devices are connected to the transfer station. A sample which has been dealt with in the transfer station and is contained in an associated reagent carrier, after it has been dealt with in the transfer station, is transferred to the rotatable wheel, by which it is pivoted to in front of an optical analysis station, where the sample which is to be analyzed, which is located in the radially outer holder, is analyzed. The rotatable wheel of this known device therefore serves only as a means of transporting the reagent carriers.

SUMMARY OF THE INVENTION

The object of the present invention is to provide an analysis system in which both the appliance costs and the costs of the individual tests are low compared to the prior art and which has an extensive test menu and a simple workflow concept, so that variable single-sample or multi-sample profiles can be carried out inexpensively.

This object is achieved by means of the analysis system, which comprises an analysis appliance and at least one system-reagent carrier, the analysis appliance having: at least one rotor which can be driven in controlled rotation, first holding devices for reagent vessels, second holding devices for sample vessels, a lifting/pivoting device which is provided with a pipetting device, can be driven in a controlled manner and can move towards and away from the rotor along a pivot path, a washing station for the pipetting device, a detector device and a control device for controlling the drive of the rotor and the drive of the lifting/pivoting device, and for controlling the operation of the pipetting device and the detector device, it being possible to place at least one sample vessel on the pivot path of the pipetting device, and the first holding devices being provided in the rotor, which forms a reaction rotor, and being designed to hold measuring cuvettes, the detector device being situated in the area of a corner position of the reaction rotor, so that the analysis takes place in a measuring cuvette which is located in the rotor, and the system-reagent carrier having at least one cuvette which is prefilled with a test-specific, preformulated, wet-chemical system reagent, as well as the measuring cuvette.

Preferably, the system-reagent carrier has a plurality of cuvettes which are arranged next to one another and are connected to one another, at least one of the cuvettes being prefilled with a test-specific, preformulated, wet-chemical system reagent.

Preferably, further cuvettes are arranged on two opposite sides of a central measuring cuvette, the opposite sides preferably being the radially inner and radially outer sides of the measuring cuvette which has been placed in a holding device, with reference to the radius of the reaction rotor. This design of a system-reagent carrier is advantageous in that the central measuring cuvette is used to hold the sample which is to be analyzed, to which the reagents, which are held in the side cuvettes, are added by pipetting. The sample which is contained in the measuring cuvette and has been mixed with the reagents can then be analyzed after the reaction rotor has been rotated to in front of the detector device.

The combination of an analysis appliance which is of relatively simple and inexpensive structure and the system.7 reagent carrier, which has one or more cuvettes which are filled individually, and in a test-specific manner, with system reagents, each cuvette being designed to carry out a single analysis operation, forms the basis of the inexpensive, flexible analysis system which allows the work to be carried out economically and inexpensively even for small to medium numbers of samples.

The cuvettes or the measuring cuvettes of each system-reagent carrier may in this case all be prefilled with the same reagent, resulting in a system-reagent carrier which is suitable for series testing of a multiplicity of different samples with regard to an analysis parameter. However, it is also possible to provide system-reagent carriers in which the cuvettes or measuring cuvettes are prefilled with different reagents, in order to carry out analyses on a single sample with regard to a multiplicity of analysis parameters.

Advantageously, the detector device has a photometric detector. In this embodiment, it is possible to carry out photometric measurements on the reaction solution, comprising sample and reagent, which is contained in the measuring cuvette to be tested.

Preferably, the second holding devices are formed by stationary holders which are arranged on a circular path which lies concentrically with respect to the pivot path of the lifting/pivoting device. This allows a very inexpensive design of the analysis appliance, in which only a single rotatable rotor, i.e. the reaction rotor, has to be provided, while the second holding devices are provided in a stationary position in the analysis appliance.

In an advantageous refinement, the second holding devices are provided on a second rotor which can be driven in controlled rotation, is of annular design and is arranged concentrically with respect to the reaction rotor. This configuration produces an analysis appliance with a higher throughput capacity, and allows the individual analyses to be carried out more flexibly.

Preferably, the second holding devices and the control device are designed in such a way that reagent containers can be inserted into the second holding devices. For certain cases, it is not only the mechanical insertion of the reagent containers into the second holding devices, but also the ability of the control unit to recognize a reagent container which has been inserted and to include this in the test process sequence, which make it possible to use specially prepared reagents which have been added to a reagent container or to use larger stores of a reagent, which is then provided in the reagent container, if the same reagent can be used, for example, for a plurality of tests.

Furthermore, it is particularly advantageous if reagent containers are provided, which are essentially compatible with the sample vessels, so that they can likewise be held by the second holding devices. This makes it possible to realize reagent containers with reagents which have been specially prepared for one analysis or various analyses (universal reagent) and which are not, or cannot be, produced at the level of system-reagent carriers. It is also possible for reagent containers of this nature to contain, for example, a dry-chemical reagent, should this be necessary for special analyses. The dry-chemical reagent should be dissolved manually or automatically prior to use. If a reagent container of this nature is inserted into one of the second holding devices together with sample vessels which are contained in other holding devices, it is preferable to provide an empty measuring cuvette in the first holding device for system-reagent carriers, for analysis purposes.

Preferably, a washing device for cleaning measuring cuvettes is provided. This washing device is advantageous in particular if the analysis uses empty measuring cuvettes into which both the sample and an externally supplied reagent are introduced, in which case the washed measuring cuvette can be used a number of times.

In another advantageous embodiment, the analysis appliance has a bound/free separation station. In this station, detectable substances which are not bound to the solid phase are separated off from the reagent, which is necessary when carrying out heterogeneous immunological tests, in which case a suitable specific solid phase is provided in the reagent, to which solid phase detectable substances are bound as a function of the analyte and in interaction with further reagent constituents.

In this case, it is particularly advantageous if the detector device has a photomultiplier for chemiluminescence measurement. This photomultiplier for chemiluminescence measurement may be provided in addition or as an alternative to a photometric detector, depending on the type of measurement or analyses for which the analysis system is to be designed.

Preferably, an evaluation unit, which evaluates the data recorded by the detector device using reference data which are stored in a memory device, is provided in the analysis system. However, the evaluation unit may also be formed by an external, commercially available computer, which is provided with suitable data and programs for evaluation and is connected to the analysis appliance of the analysis system via an interface.

If the analysis system is provided with an evaluation unit, a display device for displaying the results supplied by the evaluation device is preferably provided.

It is also possible to provide a printer device for printing out the results supplied by the evaluation device.

In a preferred configuration, the cuvettes are each closed off by means of a pierceable membrane. This ensures that the cuvettes are hermetically sealed until the analysis begins, with the result that the shelf life of the reagents contained in the cuvettes is increased noticeably, and therefore the storability of the system-reagent carriers is improved. Furthermore, it becomes possible to assess the condition of the reagent prior to measurement, making a subsequent diagnostic assessment even more certain.

The cuvettes or the system-reagent carrier may be provided with a machine-readable identification code for the respective reagent contained therein, and the analysis appliance may have a device for reading this identification code. This results in a higher level of automation when carrying out analyses, since each measuring cuvette which is to be filled with the sample, or the system-reagent carrier of this cuvette, is automatically detected, and the control device of the analysis appliance, as well as the evaluation device, are able to further process the data obtained from the reading device concerning the nature of the reagent contained in the corresponding measuring cuvette or in the corresponding system-reagent carrier and therefore concerning the test which is to be carried out with this reagent.

It is also particularly advantageous if the system-reagent carrier or the measuring cuvettes are in each case provided with a manufacturer identification coding or a manufacturer identification code, and if a recognition and decoding device is provided for this coding or code, the reading device advantageously being designed so that it can also read the manufacturer identification coding. In this way, it is possible to prevent system-reagent carriers or measuring cuvettes which are unsuitable for this analysis system from being used, since under certain circumstances this could lead to incorrect analysis results, and consequently the reliability of the analysis is increased further. Suitable coding may, for example, be effected mechanically (key-lock principle), electrically, electronically or optically, in which case the coding may also comprise an element which is protected in a different way, such as for example a trademark or a protected design element.

If the measuring cuvettes of a system-reagent carrier or individual system-reagent carriers are in each case connected to one another by means of desired breaking points, it is possible, when required, to separate individual or a plurality of measuring cuvettes from the system-reagent carrier or to separate system-reagent carriers from one another if, for example, only a few measuring cuvettes or system-reagent carriers are required for the tests which are to be performed.

The invention furthermore relates to an analysis appliance, in particular for an analysis system according to the invention, having at least one rotor which can be driven in controlled rotation, first holding devices for reagent vessels, second holding devices for sample vessels, a lifting/pivoting device which is provided with a pipetting device, can be driven in a controlled manner and can move towards and away from the rotor along a pivot path, a washing station for the pipetting device, a detector device and a control device for controlling the drive of the rotor and the drive of the lifting/pivoting device and for controlling the operation of the pipetting device and the detector device, it being possible to place at least one sample vessel on the pivot path of the pipetting device, and the rotor being designed to hold at least one measuring cuvette, in which analysis appliance the first holding devices are provided in the rotor, which forms a reaction rotor, and are designed to hold measuring cuvettes, and the detector device is situated in the area of a corner position of the reaction rotor, so that the analysis takes place in a measuring cuvette located in the rotor.

Advantageous refinements of the analysis appliance, which correspond to the appliance-specific advantageous refinements of the analysis system, are given.

The invention furthermore relates to a system-reagent carrier, in particular for an analysis system according to the invention, having at least one cuvette which is prefilled with a test-specific, preformulated, wet-chemical system reagent, the cuvette being provided with a machine-readable identification code for the reagent contained in the particular cuvette, and the analysis appliance having a device for reading the identification code, in which system-reagent carrier the cuvette or the system-reagent carrier is provided with a manufacturer identification coding which can be read and evaluated by a reading device of an associated analysis appliance.

An alternative system-reagent carrier is distinguished by the fact that a plurality of cuvettes, which are arranged next to one another and are connected to one another, are provided, at least one of the cuvettes being prefilled with a test-specific, preformulated, wet-chemical system reagent.

Preferably, a system-reagent carrier according to the invention is designed in such a way that a central cuvette, which is designed as a measuring cuvette, is provided, and that at least one further cuvette is provided in the system-reagent carrier at least on one side of the central cuvette, next to the top opening thereof, which further cuvette forms a holding chamber for a system reagent, the central cuvette and the further cuvette(s) forming a cuvette arrangement.

Advantageous refinements of the system-reagent carrier, which correspond to the refinements of the analysis system which are specific to the system-reagent carrier, are given.

DESCRIPTION OF THE PREFERRED EMBODIMENTS

Figure 1:
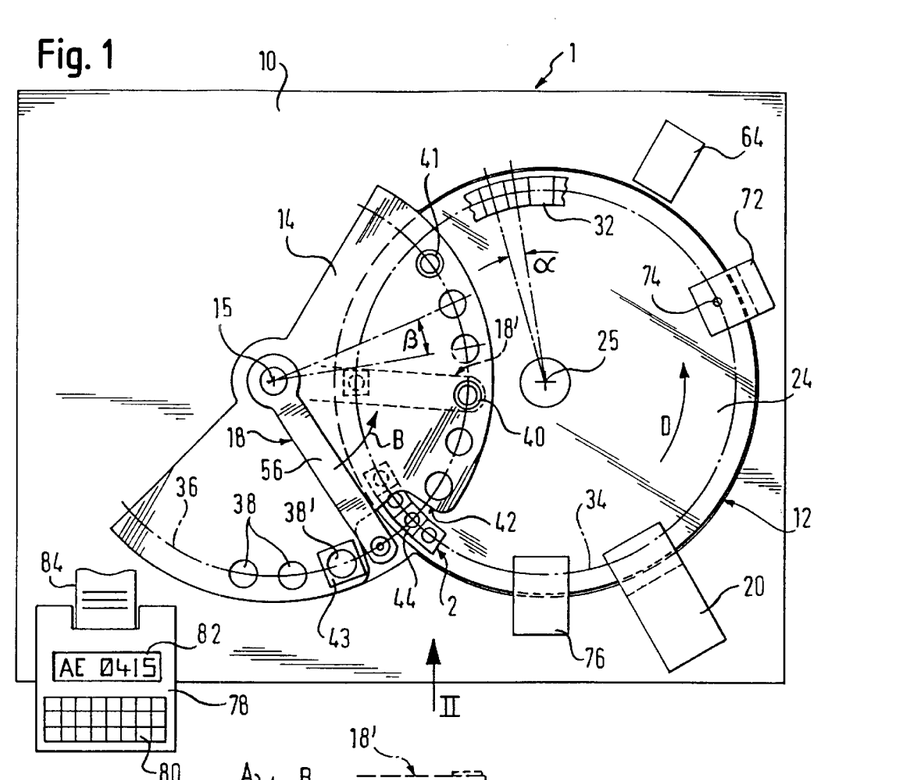
FIG. 1 shows a diagrammatic plan view of an analysis system according to a first embodiment of the invention.

The analysis system which is shown in FIG. 1 and is used for medical analysis work comprises an analysis appliance 1 with a housing 10 and at least one system-reagent carrier 2.

Figure 2:
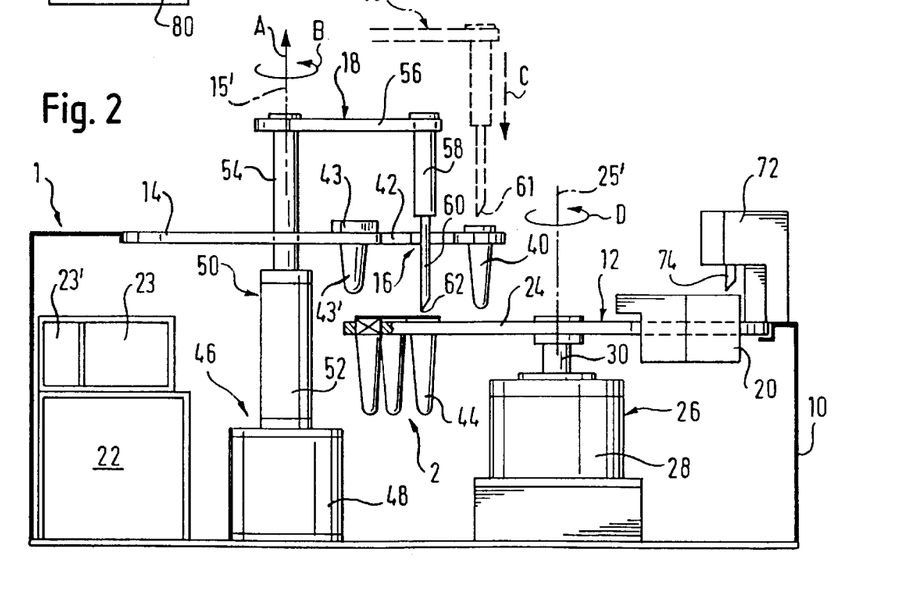
FIG. 2 shows a sectional side view of an analysis system according to the first embodiment of the invention, in the direction of arrow II in FIG. 1.

The principal components of the analysis appliance 1 are a reaction rotor 12, a holding part 14 with second holding devices 38, for sample vessels 40, a lifting/pivoting device 18 which is provided with a pipetting device 16, a washing station 43 for the pipetting device 16, a detector device 20 and a control device 22 (FIG. 2).

The reaction rotor 12 comprises a rotating holding part 24 which, in the embodiment shown in FIGS. 1 and 2, is designed as a rotatable disc, but may also be designed as a rotatable ring. The rotation plane in which the rotating holding part 24 rotates is horizontally oriented.

The rotating holding part is driven in controlled rotation by means of a drive 26, the drive 26 having a stepper motor 28 which advances the rotating holding part 24 by a predeterminable angle of rotation a at each rotation step. Via a motor shaft 30, the stepper motor 28 is connected to the center of the rotating holding part 24. The motor shaft 30 can rotate about an axis 25' which runs vertically through the center 25. As an alternative to the stepper motor 28, it is also possible to provide a different drive which is provided with a control unit which allows accurate angular orientation of the rotating holding part 24.

In the case which is not shown in the figures, in which the rotating holding part is designed as a ring, the motor shaft may be provided with a pinion which meshes with a gearwheel on the external or internal circumference of the annular rotating holding part or of an annular gearwheel which is connected to the holding part.

The rotating holding part 24 is provided with first holding devices 32 for one or more system-reagent carriers 2, the first holding devices 32 lying on a circular path 34 which is concentric with respect to the rotating holding part 24, and the first holding devices 32 lie close to the circumference of the rotating holding part 24.

On its top side, the housing 10 of the analysis appliance 1 is also provided with the holding part 14 for the sample vessels 40, which is likewise horizontally oriented. In the embodiment shown in FIGS. 1 and 2, the contour of the holding part 14 is substantially in the form of a sector of a circle. As an alternative, the holding part 14 may also be designed in the form of a circle, of a ring or of a segment of a circle. The holding part 14 is arranged at a higher level than the rotating holding part 24. The holding part 14 is provided with the second holding devices 38, which are arranged on a circular path 36, having the center 15, which is concentric with respect to the holding part 14, which is in the form of a sector of a circle. The center 15 is at a distance from the center 25 of the rotating holding part 24, the distance between these two centers or middle points 15 and 25 being less than or equal to the sum of the radius of the circular path 34 and the radius of the circular path 36, so that the circular paths 34 and 36 intersect one another.

In the area of an intersection between the two circular paths 34 and 36, the holding part 14 is provided with a radially inwardly directed cutout 42 on the circumference which, in the plan view shown in FIG. 1, allows vertical access to the measuring cuvette 44, which is located at the position of this intersection of the circular paths 34 and 36, of the system-reagent carrier 2 which is held in the rotating holding part 24 or to further cuvettes of this system-reagent carrier 2.

The pipette-washing station 43, by means of which the pipetting device 16, and in particular the pipette tubes 16, can be rinsed, so that they are cleaned and ready for a further analysis operation, is provided at the location of a holding device 38' which is adjacent to the cutout 42 in the holding part 14. The pipette-washing station 43 may, for example, comprise a washing vessel 431 which can be filled or emptied with a washing liquid via an inlet and outlet (not shown).

In the center 15 of the circular path 36, the lifting/pivoting device 18 is mounted in such a way that it can pivot about the pin 15 and can be moved vertically along the vertical axis 15' located in the center 15.

The lifting/pivoting device 18 comprises a lifting/pivoting drive 46, which has a motor 48 which is preferably designed as a stepper motor, in order to pivot the lifting/pivoting device 18 about the axis 15', preferably in equidistant steps, each step corresponding to an angle β which corresponds to the arc distance between two adjacent second holding devices 38.

The lifting/pivoting device 46 furthermore has a piston/cylinder unit 50, which allows the lifting/pivoting device 18 to move vertically. In FIG. 2, by way of example, the cylinder 52 is driven to make the pivoting movement by a motor shaft of the motor 48. The piston 54, which projects upwards out of the housing 1 and passes through the center 15 of the holding part 14, is thus made to pivot by the motor 48 and is driven vertically by the piston 52.

At its upper, free end, the piston 54 is provided with an arm 56 which extends substantially horizontally and away from the axis 15' substantially in the radially outward direction. The arm 56 extends in the radial direction to approximately as far as the circular path 36, or slightly beyond this path. At the point where the arm 56 intersects the circular path 36 (as seen in the plan view shown in FIG. 1), there is a pipette holder 58, which extends downwards from the arm 56, towards the surface of the holding part 14, and a pipette tube 60, which is preferably exchangeable, is fitted at the bottom free end of this pipette holder.

At its bottom, free end, the pipette tube 60 is narrowed so as to form a tip 62. The pipetting device 16 is provided with a suction device (not shown), which, inside the pipette tube 60, is able to generate a subatmospheric pressure or a superatmospheric pressure in order to suck in or eject fluid into or out of the pipette tube 60.

FIG. 1 also diagrammatically depicts a washing device 72 for the measuring cuvettes 44, 44', 44", by means of which device used measuring cuvettes can be emptied and rinsed when required. To this end, the washing device 72 has a vertically displaceable washing tube 74, which is designed in a similar way to the pipetting tube 60 and is provided with a bottom tip in order to pierce the membrane 47. The washing device 72 can be used in particular to clean empty measuring cuvettes 44 which are used to carry out analyses with reagents which are removed from an external reagent container 41.

The analysis appliance 1 shown in FIG. 1 also has a bound/free separation station 76, which is only diagrammatically depicted in FIG. 1. The bound/free separation station may be designed in a similar way to the washing device 72 and may likewise be provided with a vertically displaceable tube (not shown), which introduces a special washing solution into a measuring cuvette and removes the solution therefrom in order to carry out a bound/free separation process. In a bound/free separation process, molecules of a substance contained in the solution to be analyzed are bound to binding partners which are specific for this substance and are on particles or on the wall of the sample vessel (bound phase) and are separated from such molecules, which float around freely in the solution (free phase). A bound/free separation process therefore represents a washing process in which the washing solution is replaced sufficiently often for essentially only bound molecules to remain in the measuring cuvette.

The analysis appliance 1 shown in FIGS. 1 and 2 also has an evaluation device 23, which is diagrammatically depicted in FIG. 2 and evaluates the data recorded by the detector device 20 using reference data which are stored in a memory device 23', which is likewise only diagrammatically depicted in FIG. 2. The detector device 20, the evaluation device 23 and the memory device 23' are to this end connected to one another in order to exchange data, in a manner which is not shown.

As can be seen from FIG. 1, the analysis appliance is provided with a terminal 78, which has a control panel 80 for operating the analysis appliance 1 and, in particular, for inputting data to the control device 22. Furthermore, a display device 82, which is used to display the results supplied by the evaluation device 23, is provided in the terminal 78. The results supplied by the evaluation device 23 may also be printed out via a printer device 84 which is likewise provided in the terminal 78.

Figure 3:
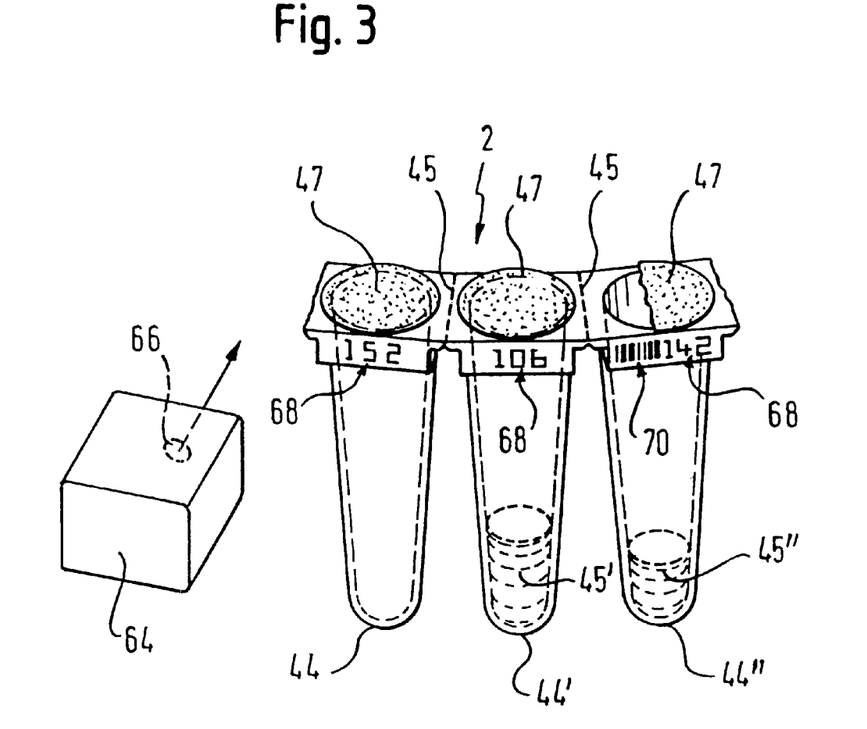
FIG. 3 shows a perspective view of a system-reagent carrier and a reading device.

The analysis appliance 1 furthermore has a reading device 64, which is located in the area of and outside the circumference of the reaction rotor 12. The reading device 64 may be designed as a plain text reader, as a pixel code reader and/or as a bar code reader, in a known way, the sensor device 66 of the reading device 64 being directed towards the reaction rotor 12. The reading direction of the sensor device 66 is directed substantially radially inward with respect to the reaction rotor 12, and the vertical position of the sensor device 66 is selected to be below or above the reaction rotor 12, in such a way that the sensor device 66 is able to read corresponding markings 68, 70 on the system-reagent carriers 2 or on the individual cuvettes or measuring cuvettes 44, 44', 44", as illustrated in FIG. 3. The markings may comprise an identification code 68 for the respective reagent and/or a manufacturer identification code 70 for identifying the manufacturer of the system-reagent carrier 2, FIG. 3 showing, purely by way of example, the identification code 68 for the particular reagent in plain text and the manufacturer identification code 70 as a bar code.

The measuring cuvettes 44, 44', 44", which are arranged next to one another in the shape of an arc corresponding to the circular path 34, of a first variant of a system-reagent carrier 2 are connected to one another at their top end section, which is of substantially rectangular design, so as to form a desired breaking point 45, in such a way that the measuring cuvettes 44, 441, 44" can be separated from one another when required and can thus be split into individual cuvettes. This allows the user to remove only the number of measuring cuvettes required for the planned analysis from this system-reagent carrier 2.

FIG. 3 furthermore shows that two of the measuring cuvettes of the system-reagent carrier 2 shown in that figure, i.e. the measuring cuvettes 44' and 44", have been prefilled, in each case to a different level, with a reagent 45' or 45", while the measuring cuvette 44 is empty and is ready for analysis of samples by means of a reagent which is not provided in the system-reagent carrier 2, which reagent is contained in an external reagent container 41, the shape of which is substantially compatible with the sample vessels 40, so that it can likewise be held by the second holding devices 38.

In the case of the system-reagent carrier 2 which is shown in FIG. 3 and in which the respective reagents are provided in individual measuring cuvettes 44', 44", it is possible to validate the reagents before carrying out an analysis on the sample which is to be introduced into the empty measuring cuvette 44. During this validation of a reagent, the reagent is measured by the detector device 20, and the measured value is compared with a reference value, making it possible to assess the condition of the reagent before the sample is analyzed.

Figure 4:
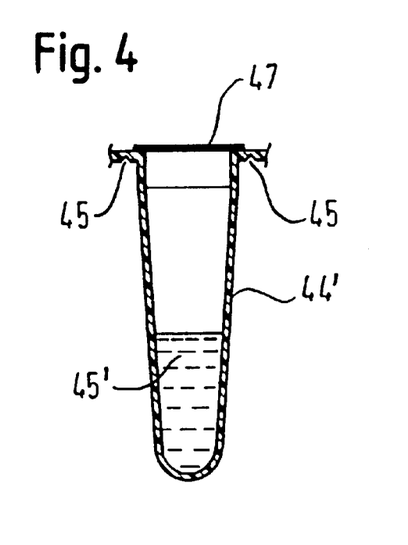
FIG. 4 shows a vertical section through a measuring cuvette of a system-reagent carrier.

FIG. 4 shows a longitudinal section through a measuring cuvette 44' which has been prefilled with the reagent 45'. Like all the other measuring cuvettes in the system-reagent carrier 2, the measuring cuvette 44' is hermetically sealed on its top side by means of a membrane 47. The membrane 47 comprises an elastically soft material which can be pierced by the tip 62 of the pipetting tube 60, and after the pipetting tube 60 has been withdrawn again, the pierced opening which is formed is substantially sealed again, to a sufficient extent for it to be impossible for any foreign bodies to penetrate into the interior of the measuring cuvette 44'.

Figure 5:
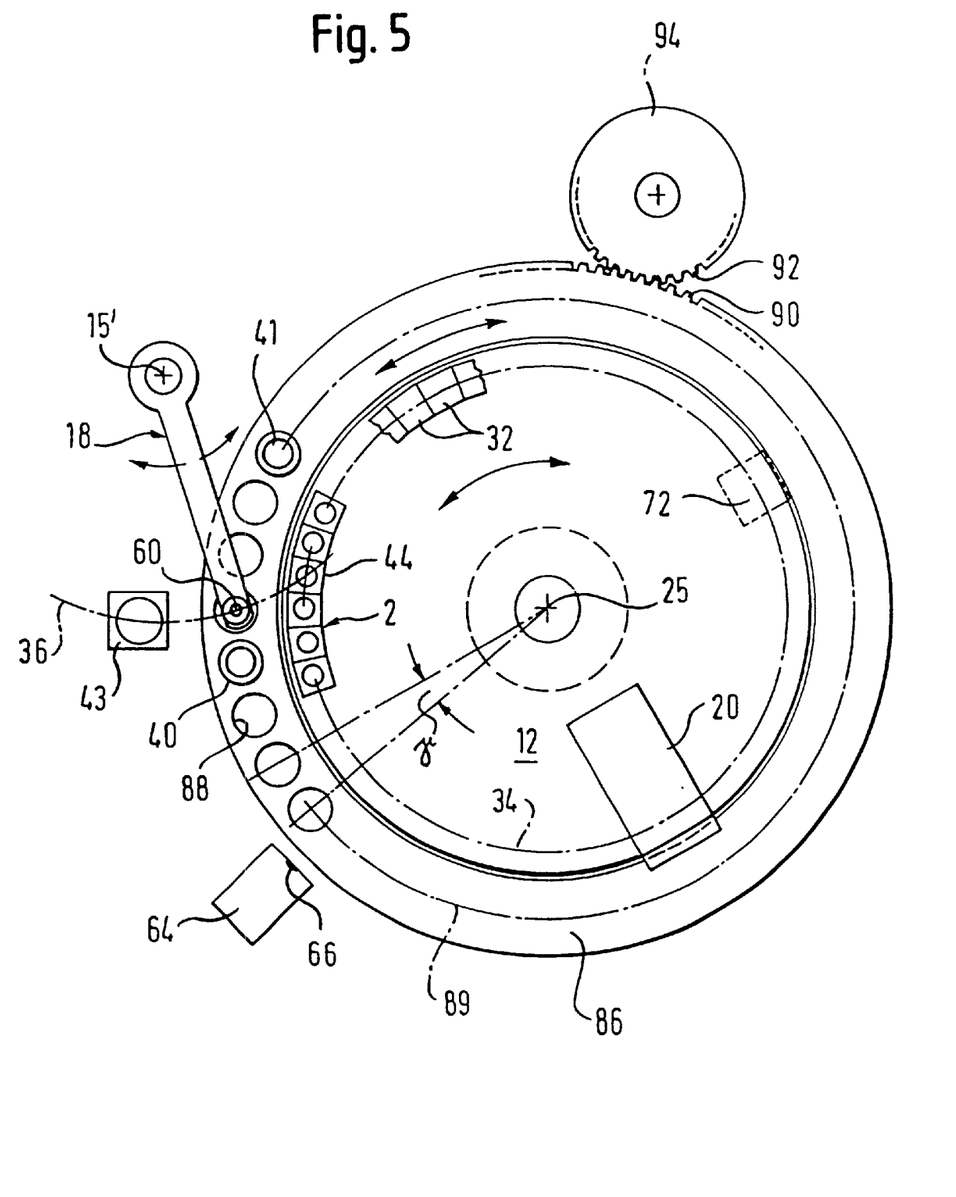
FIG. 5 shows a plan view of part of an analysis system according to a second embodiment of the invention.

FIG. 5 shows a second embodiment of the analysis system of the present invention, those components of the analysis system which correspond to those of the first embodiment being denoted by the same reference numerals.

In the second embodiment, the reaction rotor 12 is designed in the same way and is provided with first holding devices 32 for system-reagent carriers 2, as has been described with reference to FIGS. 1 and 2. The reaction rotor 12 is surrounded by an annular second rotor 86, which has holders 88 for the sample vessels 40 and for the reagent containers 41, which are of compatible design. The annular second rotor 86 is arranged concentrically with respect to the reaction rotor 12, so that its center of rotation likewise lies in the center of rotation 25 of the reaction rotor 12.

On its external circumference, the annular second rotor 86 is provided with toothing 90 which engages with the toothing 92 of a drive pinion 94 of a drive unit (not shown) for the second rotor 86. The drive unit for the pinion 94, like the drive 26 of the reaction rotor 12, preferably has a stepper motor which advances the second rotor 86 by an angle γ each time. The angle γ in this case corresponds to the arc distance between two adjacent holders 88, the center points of the holders 88 lying on a circular path 89 around a vertical axis running through the center 25. In the embodiment shown in FIG. 5, the reaction rotor 12 and the second annular rotor 86 lie in a single plane (the plane of the drawing in FIG. 5); however, they may also be offset in the vertical direction with respect to one another.

In this embodiment, the lifting/pivoting pipettor 18 is mounted outside the circumference of the second annular rotor 86, in such a manner that it can pivot about an axis 15'. The technical design of the lifting/pivoting pipettor 18 corresponds to that of the first exemplary embodiment. As in the first embodiment, the pipetting tube 60 of the lifting/pivoting pipettor 18, during pivoting, runs on a circular path 36.

The circular path 36 intersects both the circular path 89, on which the holders 88 of the annular second rotor 86 lie, and the circular path 34, on which the first holding devices 32 for the system-reagent carriers 2 are provided. The locations of the intersections between the circular path 36 and the circular paths 89 and 34 each form stopping points for the stepper drive of the annular second rotor 86 or of the reaction rotor 12, in such a manner that a sample vessel 40 or a reagent container 41, or a measuring cuvette 44, can come to rest at these intersection points when the respective drive comes to a standstill.

The pipette-washing station 43, which is designed as described in the first embodiment, lies on the circular path 36, outside the circumference of the annular second rotor 86.

The detector device 20, which is only diagrammatically depicted in FIG. 5, and the cuvette-washing station 72, which is likewise only diagrammatically depicted, are designed in a similar way to the first embodiment, their respective positions being adapted to the changed spatial details of the second embodiment, as can be seen from FIG. 5. The diagrammatically depicted reading device 64 is arranged outside the external circumference of the annular second rotor 86, and its sensor device 66 is directed radially inwards, so that the code information 68, 70 which is provided on the system-reagent carriers 2 can be read from outside the annular second rotor 86.

Since, in the second embodiment, the lifting/pivoting device 18 has to cover significantly shorter pivot paths, i.e. generally only has to cover pivot paths between a position above the center of a holder 88 on the annular second rotor 86 and the adjoining position above a measuring cuvette 44 of the system-reagent carrier 2 or the adjoining position above the pipette-washing station 43, it is possible for the individual analyses to proceed more flexibly than in the analysis system of the first embodiment.

One method of operation of the analysis system according to the invention will now be explained in more detail with reference to FIGS. 1 and 2. The lifting/pivoting device 18 moves out of its at-rest position, which is shown in solid lines, to a sample vessel 40 which contains the sample to be analyzed, in that the lifting/pivoting device initially moves vertically upwards (arrow A) and is then pivoted counterclockwise, in the direction of arrow B, into the position 18' which is shown in dashed lines. Then, the lifting/pivoting device 18 is lowered in the direction of arrow C, the pipetting tube 60 entering sufficiently far into the sample vessel 40 for the opening 61 provided at the free end of the pipetting tube 60 to dip into the sample contained in the sample vessel 40. Then, by means of the suction device (not shown in the figures), of the pipetting device 16, a predetermined amount of sample is sucked into the pipetting device 16, this suction operation being controlled by the control device 22.

After this, the lifting/pivoting pipettor 18 is raised again in the opposite direction to the arrow C and is pivoted back clockwise, in the opposite direction to the arrow B, until the pipetting tube 60 is located above the measuring cuvette 44, which lies at the intersection of the circular paths 34 and 36, of the system-reagent carrier 2. Then, the lifting/pivoting pipettor 18 is lowered back in the direction of arrow C, the tip 62 of the pipetting tube 60 piercing the membrane 47 of the measuring cuvette 44, so that the opening 61 of the pipetting tube is situated inside the measuring cuvette 44. Then, the predetermined amount of sample which has been sucked in is ejected from the pipetting device 16 through the opening 61, into the measuring cuvette 44, so that the sample and the reagent located in the measuring cuvette 44 come into contact with one another.

The lifting/pivoting pipettor 18 is then raised again in the direction of the arrow A and is pivoted to the pipette-washing station 43, where the pipetting device 16 is cleaned as a result of the pipetting tube 60 being lowered into the washing fluid situated in the pipette-washing station 43 and as a result of the washing fluid being sucked up and ejected a number times by means of the suction device. Then, the lifting/pipetting device 18 moves back into the at-rest position which is represented by solid lines.

After the pipetting tube 60 has been removed from the measuring cuvette 44, the sample and the reagent situated in the measuring cuvette 44 are mixed with one another in a known way, and then the reaction rotor 12 rotates counterclockwise, in the direction of the arrow D, until the measuring cuvette 44 has reached the detector device 20, where the photometric analysis of the mixture of reagent and sample contained in the measuring cuvette 44 takes place in a known way.

The data recorded by the detector device 20 is then transmitted to the evaluation device 23, where it is evaluated in a manner known per se using calibration data stored in the memory device 23', whereupon the data recorded by the evaluation device 23 are transmitted to the display device 82 and/or the printer 84.

The information concerning the reagent contained in the measuring cuvette 44 is passed to the evaluation device 23 by the reading device 64 which, when the measuring cuvette 44 moves past the reading device 64, reads the identification code which has been applied to the measuring cuvette 44 and transmits it to the memory device 23'. Since the angle of rotation between the reading device 64 and the location of analysis (the lower intersection of the two circular paths 36, 34 in FIG. 1) is known, a step counter, which adds or subtracts (depending on the direction of rotation) the movement steps of the reaction rotor 12, can be used to continuously record the precise position of each measuring cuvette which is held in the reaction rotor, so that in this way it is possible to accurately identify the measuring cuvette 44 which is located at the analysis site (in the detector device 20).

In the case of analysis using bound/free separation, by way of example a finely dispersed magnetic particle solution as the solid phase, together with first antibodies, is used as the first reagent. A second reagent contains a label with a second antibody. A third reagent contains a substrate or a detection solution. Should it be necessary, it is also possible to provide a pretreatment solution as a further reagent. The above-mentioned reagents are each contained in a measuring cuvette of a system-reagent carrier 2. As an alternative, one of the cuvettes, instead of being prefilled with the first reagent (e.g. coated magnetic particles), may also be directly coated with a suitable binding partner. A universal reagent may also be provided as the third reagent (substrate or detection solution). The detector (e.g. photomultiplier for chemiluminescence measurement) is to be selected as a function of the label used.

The above-described method of operation of the analysis system according to the invention serves only to explain the theoretical principles of operation. Fundamentally, however, other methods of operation are also possible, such as for example pipetting from measuring cuvette to measuring cuvette, which is carried out, for example, in the case of a test which uses a plurality of reagents, the sample initially being pipetted into a first reagent, then mixed and subsequently subjected to photometric measurement, and then, for example, a second reagent from another measuring cuvette is pipetted into the first measuring cuvette containing the sample and the first reagent, and then these substances are mixed again and subsequently subjected to photometric measurement once again. Other methods of operation include, for example, pipetting a reagent from a reagent container which is situated in a holding device for sample vessels into an empty measuring cuvette, and then adding a sample by pipetting. It is also possible to provide a universal reagent which can be used for a large number of different tests.

Figure 6:
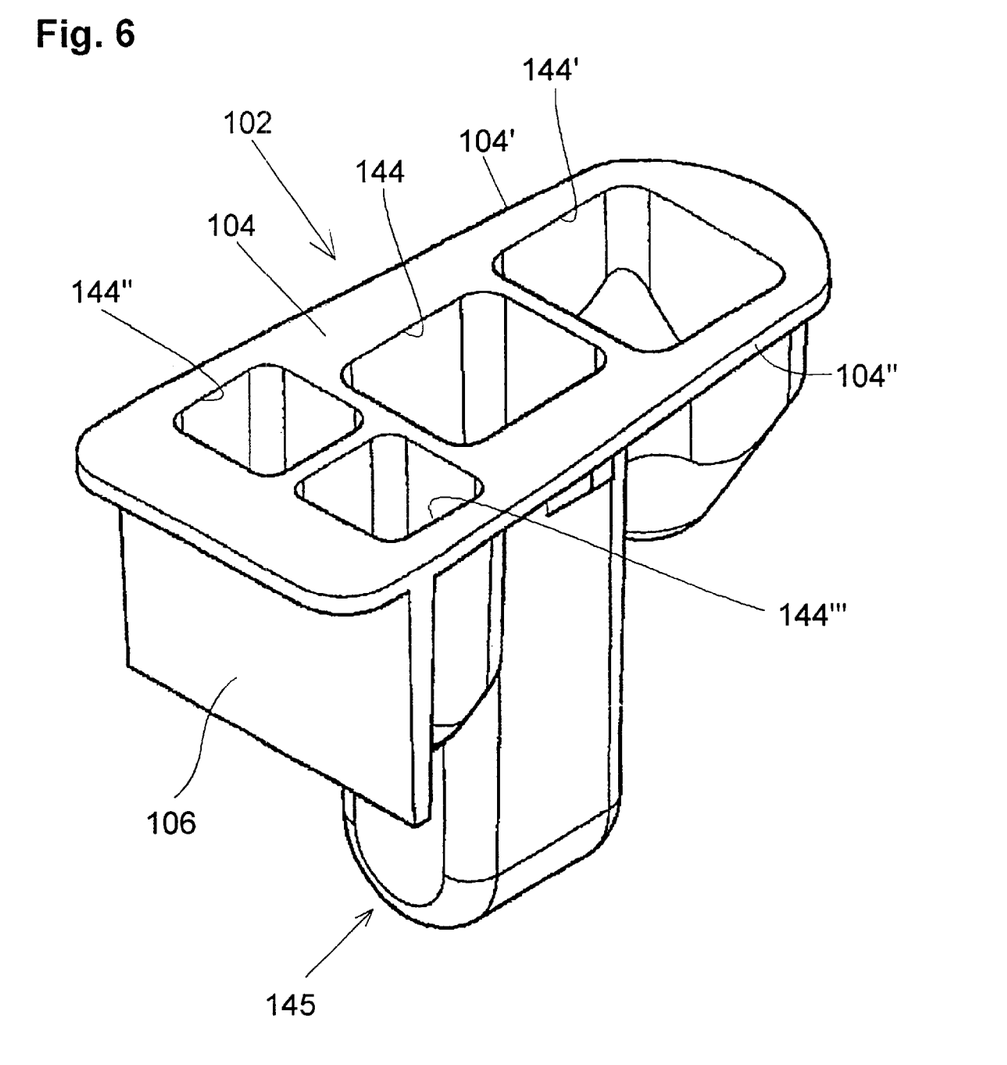
FIG. 6 shows a perspective view of an alternative system-reagent carrier.

FIG. 6 shows an alternative configuration of a system-reagent carrier 102, which comprises a plurality of chambers or cuvettes 144, 144', 144", 144'". In this case, there is a central cuvette 144 which is longer than the further cuvettes 144', 144", 144'" and which projects downwards beyond these further cuvettes. The central cuvette 144 serves as the measuring cuvette and is designed to be held by a first holding device 32 of the reaction rotor 12. The further cuvettes 144' 144", 144'" are arranged on two opposite sides of the measuring cuvette 144, next to its opening.

The individual cuvettes 144, 144', 144", 144'" are connected to one another by means of a frame 104 which, at the same time, forms a top surface in which the openings of the cuvettes are formed. In plan view, the frame 104 is essentially in the shape of a trapezium, i.e. the two longitudinal sides 104', 10" of the frame 104 run at an acute angle with respect to one another. In this way, it is possible to insert a plurality of system-reagent carriers 102 next to one another into the holding devices 32 of the reaction rotor 12, in a manner resembling slices of cake. In this case, the cuvette 144' which lies on one side of the measuring cuvette 144 lies radially inside the measuring cuvette 144, with respect to the reaction rotor, and the cuvettes 144", 144'" arranged on the other side of the measuring cuvette 144 lie radially outside the measuring cuvette 144.

On its radially outer side, the system-reagent carrier 102 is provided with a side panel 106 which extends substantially vertically and is suitable for application of the identification code 68 and of the manufacturer identification coding 70.

In the use position, the chambers or cuvettes 144', 144", 144'" are filled with reagents, while the measuring cuvette 144 is empty or may likewise be filled with a reagent. The filled system-reagent carrier 102 is sealed, in the manner described above, by means of a membrane which comprises, for example, a layer of silicone which has been applied to the top planar surface of the frame 104.

At least in its lower area 145, which projects beyond the cuvettes 144', 144", 144'" the measuring cuvette 144 is designed in such a way that it applies little or no measurement resistance to the measurement principle of the detector device 20, so that a measuring section is formed at least in this area of the measuring cuvette 144.

When using the system-reagent carrier 102, the step width of the stepper motor of the reaction rotor and/or of the lifting/pivoting device 18 is set in such a way that the pipetting device 16 can approach the individual chambers or cuvettes 144, 144', 144", 144'" without problems.

The invention is not limited to the above exemplary embodiments, which serve merely to provide a general explanation of the core idea of the invention. The device according to the invention, as well as the operating methods described, may also adopt other forms from those described above within the context of the scope of protection. In particular, the device may have features which represents a combination of the particular individual features of the claims.

The description and the drawings serve merely to improve comprehension of the invention, and are not intended to limit the scope of protection.

What is claimed is:

1. An analysis system for analysis work for carrying out clinical, chemical, and immunological analyses, comprising:

at least one system-reagent carrier (2; 102), the system-reagent carrier (2; 102) having at least one cuvette (44', 44"; 144', 144", 144'") which is pre-filled with a test-specific, pre-formulated, wet-chemical system reagent (45', 45"), the at least one system-reagent carrier having a first, machine-readable identification code (68) provided on the system-reagent carrier (2; 102) for reagents contained in the system-reagent carrier (2; 102) and a second identification code (70) provided on the system-reagent carrier (2; 102) for identifying the manufacturer of the system-reagent carrier (2; 102); and an analysis appliance (1) including:
first holding devices (32) for system-reagent carriers,
second holding devices (38) for sample vessels (40),
a pipetting device (16),
a detector device (20),
a control device (22), and
a reading device (64) for reading the first, machine-readable identification code (68) provided on the system-reagent carrier (2; 102) for reagents contained in the system-reagent carrier (2; 102) and the second identification code (70) provided on the system-reagent carrier (2; 102) for identifying the manufacturer of the system-reagent carrier (2; 102) whereby the reading device (64) reads and evaluates the identification codes (68, 70) in order to identify the system-reagent carrier (2; 102) with the reagents contained therein and in order to exclude unsuitable system-reagent carriers from being used.

2. The analysis system according to claim 1, including:
a reaction rotor (12) having a radius;
a holding device arranged with respect to the radius of the reaction rotor (12);
a central measuring cuvette (44; 144) which is part of a system-reagent carrier placed in the holding device; and
a plurality of cuvettes arranged on two opposite sides of a central measuring cuvette;
the system-reagent carrier having a plurality of cuvettes (44, 44', 44"; 144, 144', 144", 144'") which are arranged next to one another and are connected to one another;
at least one (44', 44"; 144', 144", 144'") of the cuvettes (44, 44', 44"; 144, 144', 144", 144'") being pre-filled with the test-specific, pre-formulated, wet-chemical system reagent (45', 45").

3. The analysis system according to claim 2 wherein:
the two opposite sides are on radially inner and radially outer sides of the measuring cuvette with respect to the reaction rotor.

4. The analysis system according to claim 1 wherein:
the detector device (20) has a photometric detector.

5. The analysis system according to claim 1 further including:
a lifting/pivoting device (18) bearing the pipetting device (16) having a pivot path; and second holding devices (38) formed by stationary holders arranged on a circular path (36) which lies concentrically with respect to the pivot path of the lifting/pivoting device (18).

6. The analysis system according to claim 5 including:
a second rotor (86) for controlled rotation, the second rotor (86) having an annular design arranged concentrically with respect to the reaction rotor (12); and
means for driving the second rotor (86) in controlled rotation;
the second holding devices (38) for sample vessels (40) provided on the second rotor (86) being of annular design and arranged concentrically with respect to a reaction rotor (12).

7. The analysis system according to claim 5 wherein:
the second holding devices (38) for sample vessels (40) enable reagent containers (41) to be inserted into the second holding devices (38).

8. The analysis system according to claim 7 wherein:
the reagent containers (41) are provided compatible to the sample vessels (40) to enable the reagent containers (41) to be held by the second holding devices (38).

9. The analysis system according to claim 1 and further including:
a washing device (72) for cleaning the measuring cuvettes (44, 44', 44"; 144).

10. The analysis system according to claim 1 wherein:
the analysis appliance (1) has a bound/free separation station (76).

11. The analysis system according to claim 1 wherein:
the detector device (20) has a photomultiplier for chemiluminescence measurement.

12. The analysis system according to claim 1 and further including:
a memory device (23') having reference data; and
an evaluation unit (23) to evaluate the data recorded by the detector device (20) using the reference data stored in the memory device (23').

13. The analysis system according to claim 12 further including:
a display device (82) for displaying the results supplied by the evaluation device (23).

14. The analysis system according to claim 12 further including:
a printer device (84) for printing out the results supplied by the evaluation device (23).

15. The analysis system according to claim 1 and further including:
pierceable membranes (47) closing off the cuvettes (44, 44', 44"; 144, 144', 144", 144''').

16. The analysis system according to claim 1 wherein:
the cuvettes (44, 44', 44") of a system-reagent carrier (2) are in each case connected to one another with connecting means; and
the connecting means includes breaking points (45).

17. Analysis appliance for an analysis system utilizing at least one cuvette (44', 44"; 144', 144", 144''') which is pre-filled with a test-specific, preformulated, wet-chemical system reagent (45', 45"), the at least one system-reagent carrier having a first, machine-readable identification code (68) provided on the system-reagent carrier (2; 102) for reagents contained in the system-reagent carrier (2; 102) and a second identification code (70) provided on the system-reagent carrier (2; 102) for identifying the manufacturer of the system-reagent carrier (2), the analysis appliance comprising:

first holding devices (32) for system-reagent carriers;
second holding devices (38) for sample vessels (40);
a detector device (20);
a control device (22); and
a reading device (64) for reading the first, machine-readable identification code (68) provided on the system-reagent carrier (2; 102) for reagents contained in the system-reagent carrier (2; 102) and the second identification code (70) provided on the system-reagent carrier (2; 102) for identifying the manufacturer of the system-reagent carrier (2; 102) wherein the reading device (64) reads and evaluates the identification codes (68, 70) in order to identify the system-reagent carrier (2; 102) with the reagents contained therein and in order to exclude unsuitable system-reagent carriers from being used.

18. The analysis appliance according to claim 17 wherein:
the detector device (20) has a photometric detector.

19. The analysis appliance according to claim 17 and further including:
a pipetting device (16); and
a lifting/pivoting device (18) bearing the pipetting device (16) having a pivot path;
the second holding devices (38) being formed by stationary holders which are arranged on a circular path (36) which is located concentrically with respect to the pivot path of the lifting/pivoting device (18) bearing the pipetting device (16).

20. The analysis appliance according to claim 17 and further including:
a reaction rotor (12) which can be driven in controlled rotation and which comprises the first holding devices (32) for system-reagent carriers;
a second rotor (86) which can be driven in controlled rotation being arranged concentric with respect to a reaction rotor (12); and
the second holding devices (38) provided on the second rotor (86) being of annular design.

21. The analysis appliance according to claim 17 wherein:
the second holding devices (38) are designed to receive a reagent container (41) inserted into the second holding device (38).

22. The analysis appliance according to claim 17 and further including:
a washing device (72) for cleaning the measuring cuvettes (44, 44', 44"; 144).

23. The analysis appliance according claim 17 wherein:
the analysis appliance (1) has a bound/free separation station (76).

24. The analysis appliance according to claim 23 wherein:
the detector device (20) has a photomultiplier for chemiluminescence measurement.

25. The analysis appliance according to claim 17 and further including:
a memory device (23') having reference data; and
an evaluation unit (23) to evaluate the data which have been recorded by the detector device (20) using reference data from the memory device (23').

26. The analysis appliance according to claim 25 and further including:
a display device (82) for displaying the results supplied by the evaluation device (23).

27. The analysis appliance according to claim 25 and further including:

a printer device (84) for printing out the results supplied by the evaluation device (23).

28. A system-reagent carrier (2; 102), for an analysis system including:

first holding devices (32) for system-reagent carriers, second holding devices (38) for sample vessels (40), a detector device (20), a control device (22), and a reading device (64);

the system-reagent carrier including:

at least one cuvette (44, 44', 44"; 144, 144', 144", 144'") which is pre-filled with a test-specific, pre-formulated, wet-chemical system reagent (45', 45");

a machine-readable identification code (68) readable by the detector device (20) for the reagents contained in the system-reagent carrier (2; 102); and an identification code (70) readable by the detector device (20) for identifying the manufacturer of the system-reagent carrier (2; 102).

29. The system-reagent carrier according to claim 28 further including:

a plurality of cuvettes (44, 44', 44"; 144, 144', 144", 144'"), arranged next to one another and connected to one another;

at least one (44', 44"; 144', 144", 144'") of the cuvettes (44, 44', 44"; 144, 144', 144", 144'") being pre-filled with a test-specific, pre-formulated, wet-chemical system reagent (45', 45").

30. The system-reagent carrier according to claim 28 further including:

a central cuvette (144) designed as a measuring cuvette;

at least one further cuvette (144', 144", 144'") in the system-reagent carrier (102) being at least on one side of the central cuvette (144), which further cuvette forms a holding chamber for a system reagent; and the central cuvette (144) and the at least one further cuvette(s) (144', 144", 144'") forming a cuvette arrangement.

31. The system-reagent carrier according to claim 28 wherein:

at least one further cuvette (144', 144", 144'") for holding system reagents is provided on each of two opposite sides of the measuring cuvette (144).

32. The system-reagent carrier according to claim 28 wherein:

the longitudinal extent of the measuring cuvette (144) projects beyond the longitudinal extent of the further cuvettes (144', 144", 144'"); and a measuring section is formed in the measuring cuvette (144).

33. The system-reagent carrier according to claim 28 wherein:

the cuvettes (44, 44', 44"; 144, 144', 144", 144'") are each closed off by means of a pierceable membrane (47).

34. The system-reagent carrier according to claim 28 wherein:

a plurality of cuvettes (44, 44', 44") are connected to one another by means of desired breaking points (45).

* * * * *

UNITED STATES PATENT AND TRADEMARK OFFICE
CERTIFICATE OF CORRECTION

PATENT NO. : 6,375,898 B1
DATED : April 23, 2002
INVENTOR(S) : Frank Ulrich It is certified that error appears in the above-identified patent and that said Letters Patent is hereby corrected as shown below:

<u>Title page,</u>
Item [75], should read -- [75] Inventor: Ulrich Frank, Moerlenbach (DE) --

Signed and Sealed this

Fourteenth Day of January, 2003

JAMES E. ROGAN
*Director of the United States Patent and Trademark Office*